United States Patent
Cox

(10) Patent No.: US 7,118,214 B2
(45) Date of Patent: *Oct. 10, 2006

(54) PRESBYOPIC VISION IMPROVEMENT

(75) Inventor: Ian G. Cox, Honeoye Falls, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 89 days.

This patent is subject to a terminal disclaimer.

(21) Appl. No.: 10/972,131

(22) Filed: Oct. 22, 2004

(65) Prior Publication Data

US 2005/0083483 A1   Apr. 21, 2005

Related U.S. Application Data

(63) Continuation of application No. 10/274,677, filed on Oct. 18, 2002, now Pat. No. 6,808,265.

(60) Provisional application No. 60/348,192, filed on Oct. 19, 2001.

(51) Int. Cl.
*G02C 7/04* (2006.01)

(52) U.S. Cl. ..................... 351/161; 177/246

(58) Field of Classification Search ............ 351/160 R, 351/160 H, 161, 177, 246
See application file for complete search history.

(56) References Cited

U.S. PATENT DOCUMENTS

| | | | |
|---|---|---|---|
| 4,637,697 A * | 1/1987 | Freeman | 351/161 |
| 5,777,719 A | 7/1998 | Williams | 351/212 |
| 5,949,521 A | 9/1999 | Williams | 351/246 |
| 6,086,204 A * | 7/2000 | Magnante | 351/212 |
| 6,095,651 A | 8/2000 | Williams | 351/246 |
| 6,280,435 B1 * | 8/2001 | Odrich et al. | 606/5 |
| 6,283,976 B1 * | 9/2001 | Portney | 606/107 |
| 6,379,005 B1 | 4/2002 | Williams | 351/211 |
| 6,379,008 B1 * | 4/2002 | Chateau et al. | 351/247 |
| 6,416,179 B1 * | 7/2002 | Lieberman et al. | 351/212 |
| 6,499,843 B1 * | 12/2002 | Cox et al. | 351/246 |
| 6,533,416 B1 * | 3/2003 | Fermigier et al. | 351/160 R |
| 6,554,425 B1 * | 4/2003 | Roffman et al. | 351/177 |
| 6,655,803 B1 * | 12/2003 | Rubinstein et al. | 351/177 |

FOREIGN PATENT DOCUMENTS

WO    01/28477 A1    4/2001

OTHER PUBLICATIONS

U.S. Appl. No. 10/078,163, filed Feb. 20, 2002, As Entitled "Method and Apparatus for Improving Vision and the Resolution of Retinal Images" (copy not enclosed).

* cited by examiner

*Primary Examiner*—Scott J. Sugarman

(57) ABSTRACT

A method of designing a contact lens or other correction for providing presbyopia correction to a patient relies on wavefront aberration measurement data for providing a best form correction. Preferably the correction is in the form of a multifocal translating style alternating vision contact lens or a simultaneous vision style correcting lens. A method for designing a correction for improving a person's vision is directed to correcting higher order aberrations in such a manner that a residual amount of the higher-order rotationally symmetric aberration is greater than a residual amount of the higher-order rotationally asymmetric aberration after the correction. A design method according to the invention is directed to correcting asymmetric higher order aberrations induced by decentering of a multifocal contact lens that has residual spherical aberration which provides increased depth of field.

1 Claim, 2 Drawing Sheets

210 — Fit trial lens; monitor WF at near and infinity; optimize metric

220 — monitor WF a function of lens decentration

230 — monitor coma in relation to spherical aberration

240 — design coma correction

FIG. 2 under fitting consideration, the position of the trial lens will be immediately in front of the patient's eye.

PRESBYOPIC VISION IMPROVEMENT

CROSS-REFERENCE TO RELATED APPLICATIONS

This is a continuation of Provisional Application Ser. No. 60/348,192, filed Oct. 19, 2001 and U.S. application Ser. No. 10/274,677, filed Oct. 18, 2002, now U.S. Pat. No. 6,808, 265 by the same inventors, and claims priority therefrom.

BACKGROUND OF THE INVENTION

1. Field of the Invention

The present invention relates generally to the field of presbyopic vision correction and, more particularly, to the use of a wavefront sensor for the measurement, design, fit and dispensing of a vision altering optic or vision correcting procedure to improve presbyopic correction and visual performance.

2. Description of Related Art

A form of age-dependent vision deterioration experienced sooner or later by 100% of the population is called presbyopia, i.e., the inability to accommodate or focus on objects close to the eye. Two well-known methods for dealing with presbyopia include alternating vision style correction and simultaneous vision style correction.

In an example of an alternating vision style correction, two (or more/multi-focal) distinct optical regions of a translating style contact lens are designed, one optimized for distance vision and the other for near vision. Typically in an alternating vision bifocal contact lens, the lens will translate on the eye such that the pupil is mostly covered by the distance viewing portion of the lens; however, when eye gaze points downward, such as when a person reads a newspaper, the lens translates on the eye such that the pupil is mostly covered by the near distance viewing portion of the lens.

Alternatively, simultaneous style vision correction has been provided through, e.g., contact lenses, IOLs, refractive surgery, etc. In this style of correction, all light from the object goes through the pupil at the same time, preferably with a 50/50 split between near distance and far distance object light. Any one of a number of refractive or diffractive bifocal or multifocal designs are used to focus light from objects ranging in the field of view from far distance (greater than about 7 m) to near distance (as close as about 0.25 m but typically about 40 cm) on the retina at the same time.

As a person gets older, not only do they lose the ability to accommodate, they also experience an increase in what are known as higher order wavefront aberrations. These include, but are not limited to, spherical aberration, coma, irregular astigmatisms (e.g. triangular astigmatism or trefoil), and others. The aberrations corrected by spectacles or single vision contact lenses are limited to defocus and astigmatism which are generally referred to as lower-order aberrations. An increase in spherical aberration brought about, for example, by advancing age, will decrease nighttime vision quality. This may manifest itself as halos or glare around headlights or other light sources. Unfortunately, for the presbyope hoping for better near distance vision with a translating-style contact lens, the correction of the spherical aberration for improved far distance, night time vision results in a decrease in near vision depth of field; i.e., the amount an object's distance can be shifted before the retinal image of the object has too much blur.

There are also vision tradeoffs for the multifocal, simultaneous style correction lens wearer. Although there are claims of excellent clinical success with a number of simultaneous vision bifocal and multifocal designs, actual published success rates with refractive and diffractive contact lenses for presbyopic correction range only from about 20% to 50% of the general presbyopic population. One of the apparent limiting factors of all current simultaneous style vision correction for presbyopia is lens misalignment; i.e., the lack of control of the centration of the lens relative to the optical axis of the patient. Unfortunately, the induced aberrations caused by the optical misalignment of the eye with the simultaneous vision correction lens reduces visual performance to the point that vision quality is unacceptable to the patient at any viewing distance.

One approach to alleviating vision performance problems is, presumably, to eliminate all optical aberrations in the eye. In the first instance, this solution may not be technically feasible, although correction of wavefront errors via customized refractive surgical techniques and/or customized contact lenses, inlays, onlays, and IOLs, for example, is becoming better understood each day. Moreover, the elimination of all optical aberrations in the eye may not be desirable. For example, reducing spherical aberration will adversely affect depth of field, as discussed above, thus some residual spherical aberration may be desirable for optimum vision quality.

Accordingly, there is a need for vision correcting methods and devices that address the aforementioned problems. In particular, methods and apparatus are needed for providing multifocal lens correction of presbyopia with improvement, or at least no degradation, of other aspects of vision quality.

SUMMARY OF THE INVENTION

The invention in general relates to methods and devices for optimizing presbyopic vision correction, preferably with a contact lens, but not limited as such and including, as appropriate, IOLs, inlays, onlays, or refractive surgery. A predominate theme of all of the embodiments of the invention is the use of a wavefront sensor in the design and fitting of alternating vision and simultaneous vision style corrective lenses, or in refractive surgery, and in balancing various aberrations to achieve the best objective vision metric possible.

An embodiment of the invention relates to a method for designing either a customized, multifocal, alternating style translating contact lens or a simultaneous vision style correcting lens, and the providing such a lens to a presbyopic patient. The method comprises the steps of positioning, with respect to a patient's eye, a multifocal trial lens that is representative of an actual lens to be provided to the patient, wherein the trial lens has a correction of approximately a distance defocus power of the patient's eye; making a first wavefront aberration measurement of the patient's eye with the trial lens in position, at a viewing distance equivalent to optical infinity; making a second wavefront aberration measurement of the patient's eye with the trial lens in position, at an artificial optical near point viewing distance; and using the first and second wavefront aberration measurements to approximate a best form wavefront correction to be applied to the contact lens, whereby the patient's presbyopic vision is improved. It will be clear to a person skilled in the art that the step of positioning the lens with respect to the patient's eye has alternative aspects. For example, if the lens to be provided is a translating style, alternating vision type contact lens, the position of the representative trial lens will be on the patient's eye. In a different aspect where the lens to be provided is a simultaneous vision style correcting lens element, the lens element can be a contact lens that will be positioned on the patient's eye; however, if the simultaneous vision style correcting lens element is an IOL, the representative trial lens will be suitably positioned in an optical path of the wavefront sensor device used to make the wavefront aberration measurement. The wavefront aberration measurements are preferably made along a central axis of the trial lens. The best form wavefront correction will provide an optimum retinal image metric, preferably a Point Spread Function (PSF) having a single intensity peak or a Strehl ratio having as large a value as possible, for example. Other retinal image metrics known to those skilled in the art can also be used. The near point viewing distance wavefront measurement should be in the range of about 30–50 cm and will typically be approximately 40 cm. For the case of a translating style, alternating vision type correcting contact lens, the near distance measurement is obtained by inducing a down gaze of the patient's eye to produce the trial lens translation similar to that of an actual translating multifocal contact lens when worn by the patient. In an aspect of this embodiment, use of the wavefront sensor in designing and fitting a translating style multifocal contact lens will allow the practitioner to monitor the retinal image metric for optimum presbyopic vision while adjusting, e.g., residual spherical aberration in the lens that will result in the best overall vision for the patient while providing an acceptable depth of field to the patient.

In another aspect of the embodiment for designing and providing a simultaneous vision type correcting lens, use of the wavefront sensor facilitates the optimum lateral, vertical, and rotational placement of the lens to optimize the retinal image metric. This can be accomplished, e.g., by adjusting the position of the patient's head and, therefore, the patient's optical axis with respect to the measurement axis of the wavefront sensor or, alternatively, utilizing a feedback loop in the wavefront sensor to determine the optimum location in the lens for aberration correction. In a related aspect, wherein a patient has had photorefractive surgery such as LASIK, for example, a retreatment may be performed to correct for misalignment or decentration of the original ablation treatment that resulted in vision degrading higher-order aberrations. Upon retreatment, the surgeon may choose not to fully eliminate the residual spherical aberration.

In another embodiment of the invention, a method for designing a lens or other correction (e.g., refractive surgery correction) to improve a patient's vision quality that is degraded by both rotationally symmetric and rotationally asymmetric aberrations involves designing the lens or the correction such that a residual amount of the rotationally symmetric aberrations are greater in magnitude than a residual amount of rotationally asymmetric aberrations, e.g., coma. Once again, exemplary metrics for evaluating the patient's visual quality include, but are not limited to, the PSF and the Strehl ratio. The amount of residual or uncorrected rotationally symmetric aberrations will vary in each patient, and guidance will be provided by the aforementioned metrics. Preferably, the distribution of light in the PSF will not contain multiple peaks.

In another embodiment, a method for designing a lens or a correction for enhancing the near vision performance of a presbyopic patient includes a design that eliminates less than the total amount of the spherical aberration in the person's visual optical system so as to increase the person's depth of field. Aspects of this embodiment include ocular corrections that apply to vision altering optics such as contact lenses, IOLs, inlays, onlays, and the like, to the cornea through laser ablation and other refractive surgical techniques, and to other components of the eye.

These and other objects and advantages of the invention will be further apparent in consideration of the drawings and the detailed description of the preferred embodiments, and in view of the appended claims defining the invention.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings, FIG. 2 is a flow chart diagram illustrating another preferred embodiment according to the invention.

DETAILED DESCRIPTION OF PREFERRED EMBODIMENTS

Figure 1:
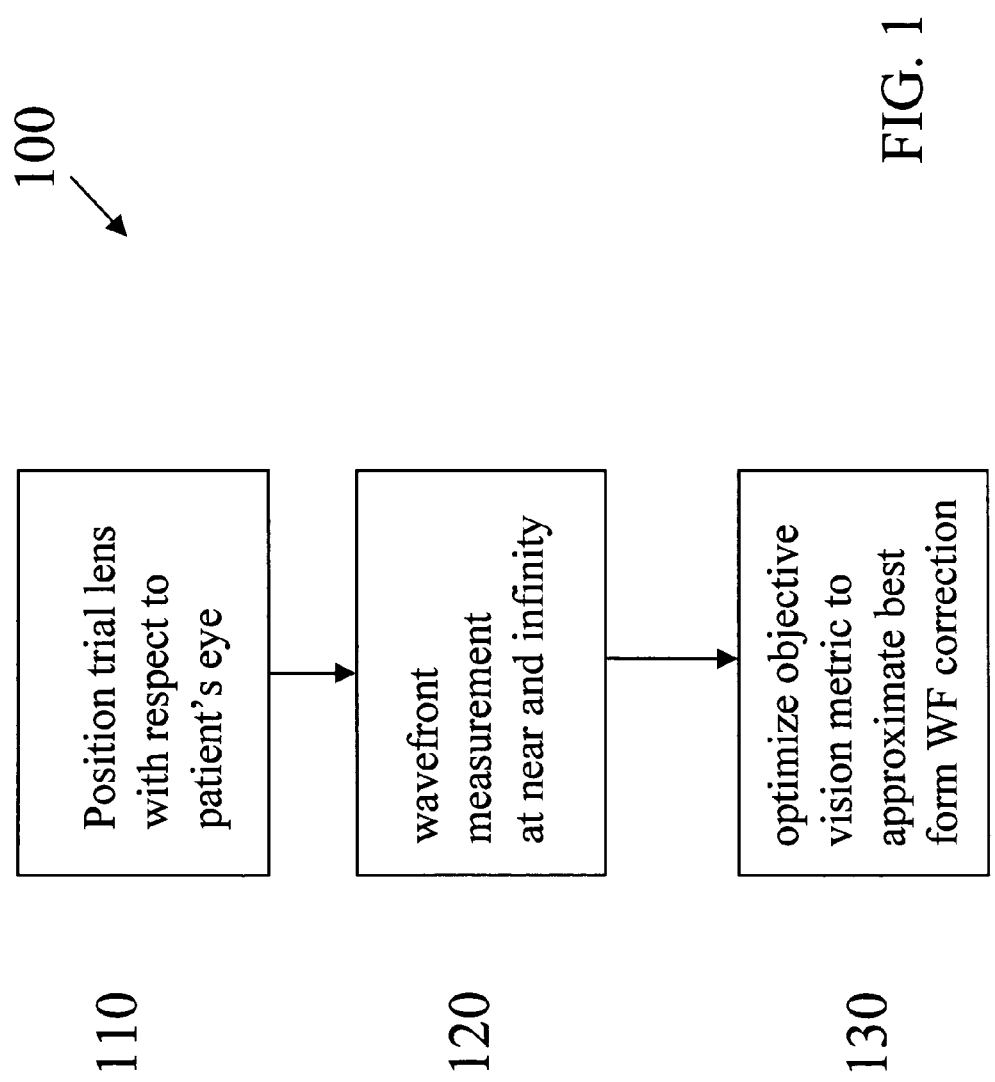
FIG. 1 is a flow chart diagram illustrating a preferred embodiment of the invention.

An embodiment of the invention describes, with reference to FIG. 1, a method 100 for designing either a customized multi-focal, translating style, alternating vision contact lens, or, a simultaneous style vision-correcting lens, and providing the lens to a patient. In step 110, a multi-focal trial lens is first positioned appropriately with respect to the patient's eye. The trial lens is representative of the customized lens ultimately to be provided to the patient, and should provide correction for the defocus aberration experienced by the patient. In an aspect of the embodiment where the lens ultimately to be provided to the patient is a translating style, alternating vision type multifocal contact lens, the appropriate positioning of the trial lens will be on the patient's eye in the form of a trial contact lens. In an alternative aspect of the embodiment where the lens to be provided to the patient is a correcting lens element not worn on the surface of the cornea such as an IOL or inlay providing simultaneous style presbyopic vision improvement to the patient, the appropriate positioning of the trial lens will be in the optical measurement path of a wavefront sensor to simulate the optical effect as if the lens element was in-situ. Wavefront aberration measurements are then made at step 120 through the trial lens in such as manner that the patient is imaging at optical infinity and at an optical near point distance, preferably 30–50 cm from the patient's eye and, more preferably, approximately 40 cm from the patient's eye. A down gaze of the patient's eye can be induced by using a front surface mirror in the measurement apparatus or by any of a number of known means, for making the near vision measurement. In step 130, the near distance and infinite distance aberration measurements are then used to approximate a best form wavefront correction to a customized lens ultimately to be provided to the patient. The best form wavefront correction is preferably determined by optimizing a retinal image metric such as, for example, a point-spread function (PSF) or a Strehl ratio. Simply, the PSF corresponds to the energy distribution in the image of a point source of light object. An optimized PSF, for instance, would have only a single intensity peak representing the light distribution of the imaged spot. The Strehl ratio can be defined as the ratio of the area under the point spread function of the actual optical system wavefront (i.e., aberrated wavefront) to that for the diffraction limited case (i.e., no wavefront aberration in the optical system). Thus a Strehl ratio of 1.0 would describe a substantially perfect optical imaging system. Further information may be obtained from the text by Warren J. Smith entitled *Modern Optical Engineering*, McGraw Hill, Inc. (1966), incorporated herein by reference.

Generally speaking, as people age their vision deteriorates. Older individuals often report poor nighttime vision. There is also a known correlation between increases in higher order aberrations and increasing age. One conclusion that can be drawn from this evidence is that poorer night vision in older individuals is due to an increase in higher order aberrations naturally experienced by older individuals. Presbyopia is an additional age-related visual deterioration. Although correcting spherical aberration tends to improve nighttime vision problems, it is well known that reducing spherical aberration reduces a person's depth of field. Thus, a presbyopic bifocal wearer may need to choose between better night vision and reduced depth of field for near distance viewing, or vice-versa. Advantageously, the inventors have recognized that in many cases a person's corrected eyesight may be better when there is some residual spherical aberration after correction. This will provide the added benefit of maintaining or increasing a depth of field for the presbyopic lens wearer. Accordingly, an aspect of the present embodiment of the invention is directed to a correction design process that involves providing a known amount of residual spherical aberration in order to improve visual quality and increase or at least maintain depth of field. Preferably, in the presence of rotationally symmetric higher order aberrations (e.g., spherical aberration) and rotationally asymmetric higher order aberrations (coma, higher order astigmatism), a method of for improving a person's vision involves providing a correction design having a residual amount of rotationally symmetric higher order aberrations that exceed the residual amount of rotationally asymmetric higher order aberrations. This is illustrated with respect to Example 1 below. This may be accomplished preferably through the design of a contact lens or an IOL, or alternatively, in an inlay, onlay, or refractive surgery procedure.

EXAMPLE 1

This example illustrates the concept that under the ability to manipulate the spherical aberration of an ocular correction, due to the ability to only change rotationally symmetric surfaces or parameters such as, e.g., a contact lens, an IOL, or a broad beam laser, it is more beneficial not to correct all of the spherical aberration when there are significant amounts of non-rotationally symmetric aberrations (e.g., coma, trefoil) present. Patient X had refractive surgery. Her measured post-operative Zernike coefficient values measured with a Zywave® (Bausch & Lomb, Rochester, N.Y.) wavefront sensor were:

| | |
|---|---|
| Z7 Coma | 0.068 |
| Z8 Coma | −0.540 |
| Z9 (Trefoil) | 0.103 |
| Z10 (Spherical) | −0.371 |
| Z11 (Spherical) | −0.782 |
| Z12 (Spherical) | −0.308 |
| Z13 (Spherical) | −0.135 |
| Z14 (Spherical) | −0.007 |
| Z15 (Secondary Coma) | −0.183 |
| Z16 (Secondary Coma) | −0.071 |
| Z17 (Secondary Coma) | 0.021 |
| Z18 (Secondary Coma) | 0.018 |
| Z19 (Secondary Coma) | 0.010 |

-continued

| | |
|---|---|
| Z20 (Secondary Coma) | −0.026 |
| Z21 (Secondary Spherical) | 0.023 |

One can see that there is significant coma and triangular astigmatism. In Table I, below, the left-most value is the multiplication factor of the Zernike coefficient Z11 that represents the majority of the measured spherical aberration. Looking at the various values of the corrected spherical aberration, it is seen that correcting all of the spherical aberration is actually deleterious to the retinal image quality as measured by the Strehl ratio. The highest Strehl ration is obtained when 25% of Z11 remains. In fact, leaving 50% of the Z11 spherical aberration results in a similar retinal image quality to correcting all of the spherical aberration as defined by the Strehl ratio.

TABLE I

| Residual Z11 | Strehl Ratio | RMS | Peak-Valley (waves) |
|---|---|---|---|
| 0.00 Z11 | 0.023 | 0.77 | 8.34 |
| 0.25 Z11 | 0.036 | 0.79 | 8.34 |
| 0.50 Z11 | 0.024 | 0.87 | 8.35 |
| 0.75 Z11 | 0.016 | 0.96 | 8.68 |
| 1.00 Z11 | 0.007 | 1.099 | 9.55 |

The optimum amount of corrected spherical aberration will vary in each eye, and may be guided by the Strehl ratio, i.e., the distribution of light within the PSF such that there are not multiple peaks, or by other appropriate retinal image quality metrics well known in the art. The remaining residual spherical aberration will have the additional benefit of enhancing the near visual performance for presbyopic patients by extending the depth of field for the patient.

It is assumed that one of the major limiting factors of all current simultaneous vision methods for correcting presbyopia is the failure to control the centration of these designs relative to the optical axis of the patient, and that the induced aberrations caused by the optical misalignment of the eye with simultaneous correction reduces the visual performance of the patient being corrected to the point that their visual quality is unacceptable to them at near or far viewing distances. There is speculation that the actual published success rates with refractive and diffractive contact lenses range from 20% to 50% of the general presbyopic population due to the centration issue. This problem is easily exasperated when the lens purposely contains residual spherical aberration as discussed above. Recognition of the centration problem gives rise to another embodiment of the invention described with reference to FIG. 2. In this embodiment 200, a wavefront sensor is used not only to measure the patient's higher order aberrations but also to monitor the fitting of a lens element subject to decentration in the person's optical system. With respect to a simultaneous style bifocal contact lens, for example, at step 210 both near distance and far distance higher order aberration measurements are made with a trial lens appropriately positioned on the patient's eye. The optimum lateral, vertical, and/or rotational placement of the simultaneous style lens is then determined at 220 to optimize a retinal image metric. The lens ultimately to be provided to the patient can then be customized in terms of location of aberration correction on the lens and/or for the proper placement of the lens on the patient's eye. In one aspect of this embodiment, the proper measurement coordinates can be explored by displacing the patient's eye relative to the measurement axis of the wavefront sensor via an adjustable chin mount or other appropriate means, or alternatively, by utilizing a feedback loop in the wavefront sensor to determine the optimum placement of the lens on or in the patient's eye. A wavefront sensor equipped with a deformable mirror, for example, as described in Williams U.S. Pat. No. 5,777,719 illustrates the basic technology for making such measurements. In an associated aspect of this embodiment shown in step 230, a trial lens having a known amount of spherical aberration is positioned with respect to the patient's eye. Decentering of the lens having spherical aberration induces coma. A customized lens corrected for this induced coma can be designed at 240 by monitoring the wavefront aberrations based on the trial lens. It will be appreciated that the lens itself need not be decentered on the patient's eye or with respect to the patient's optical axis as the decentering, which creates spherical aberration, is equivalent to a properly positioned lens on the patient's eye with residual spherical aberration in the lens. Alternatively, this result may also be accomplished in a refractive surgery retreatment procedure where less than the entire residual spherical aberration is corrected.

Notwithstanding the preferred embodiments specifically illustrated and described herein, it will be appreciated that various modifications and variations of the instant invention are possible in light of the description set forth above and the appended claims, without departing from the spirit and scope of the invention.

I claim:

1. A lens for improving a subject's vision based on an objective vision metric, comprising:
   a customized multifocal surface based upon a wavefront measurement at a far target distance and a wavefront measurement at a near target measurement, wherein the customized surface has a shape that provides a residual amount of a rotationally symmetric aberration that is greater than a residual amount of an asymmetric aberration.

* * * * *